(12) United States Patent
Bartov

(10) Patent No.: US 7,315,642 B2
(45) Date of Patent: Jan. 1, 2008

(54) SYSTEM AND METHOD FOR MEASURING THIN FILM THICKNESS VARIATIONS AND FOR COMPENSATING FOR THE VARIATIONS

(75) Inventor: Avishay Bartov, Hod-Hasharon (IL)

(73) Assignee: Applied Materials, Israel, Ltd., Rehovot (IL)

( * ) Notice: Subject to any disclaimer, the term of this patent is extended or adjusted under 35 U.S.C. 154(b) by 783 days.

(21) Appl. No.: 10/778,664

(22) Filed: Feb. 12, 2004

(65) Prior Publication Data

US 2005/0179910 A1 Aug. 18, 2005

(51) Int. Cl.
*G06K 9/00* (2006.01)
*H01L 31/0232* (2006.01)
*B44C 1/22* (2006.01)

(52) U.S. Cl. ............ 382/145; 382/274; 257/437; 216/85

(58) Field of Classification Search ............... 382/145, 382/148, 162, 168, 190, 274; 356/504, 632, 356/43; 451/6, 41; 257/437, E21.029, 640, 257/649, E21.269, E23.167, E31.115, E27.128, 257/E21.23; 216/85, 89, 88; 374/128, 126, 374/1, 2, 121, 110, 124; 219/502; 355/67
See application file for complete search history.

(56) References Cited

U.S. PATENT DOCUMENTS

| 5,433,651 | A | * | 7/1995 | Lustig et al. | 451/6 |
| 5,838,448 | A | * | 11/1998 | Aiyer et al. | 356/632 |
| 6,674,890 | B2 | * | 1/2004 | Maeda et al. | 382/149 |
| 6,798,529 | B2 | * | 9/2004 | Saka et al. | 356/630 |
| 7,027,640 | B2 | * | 4/2006 | Park et al. | 382/152 |
| 7,171,036 | B1 | * | 1/2007 | Liu et al. | 382/145 |

\* cited by examiner

*Primary Examiner*—Sheela Chawan
(74) *Attorney, Agent, or Firm*—Tarek N. Fahmi

(57) ABSTRACT

A method for measuring thin film thickness variations of inspected wafer that includes an upper non-opaque thin film. The method including (i) scanning the wafer and obtain wafer image that includes die images each of which composed of pixels, (ii) identifying regions in a first die image and obtain first intensity measurements of the respective regions, (iii) identifying corresponding regions in a second die image and obtain second intensity measurements of the respective regions, (iv) processing the first intensity measurements and the second intensity measurements to obtain signal variations between the second intensity measurements and the first intensity measurements, whereby each calculated signal variation is indicative of thickness variation between a region in the second die and a corresponding region in the first die.

25 Claims, 4 Drawing Sheets

SYSTEM AND METHOD FOR MEASURING THIN FILM THICKNESS VARIATIONS AND FOR COMPENSATING FOR THE VARIATIONS

FIELD OF THE INVENTION

This invention relates to signal variation measurement technique for detecting thin film thickness variations across a wafer or reticle.

BACKGROUND OF THE INVENTION

Related Art

Interference involving multiple reflections is known in the art. This phenomenon is described at "Fundamentals of Optics", F. A. Jenkins and H. E. White, 4th edition, 1976, pages 286-314. The interference results from multiple reflections of light between two substrates of a thin layer (or film) of transparent material. In other words, a single beam of radiation that is directed towards a thin layer of transparent material that is followed by an object that has a refractive index different from the film causes multiple beams of radiations to be reflected from the thin layer. If the object is transparent or partially transparent the single beam of radiation may result in additional multiple transmitted beam of radiations. The multiple reflected beams of radiations undergo distinct optical paths and generate interference patterns.

This phenomenon may occur in bright field inspection systems for inspecting various objects such as semiconductor wafers. In many cases a thin layer of dielectric material coats the inspected layer of interest. A typical dielectric layer is made of SiO2, silicon nitride, photo resists and so on. Due to the difficulties of producing a uniform layer across the entire wafer during chip manufacturing process, small thickness changes may exist for different dies. These thickness variations are insignificant for the electrical performance of the IC's but may cause significant reflectivity changes in the course of bright field inspection. When wafer inspection includes a die-to-die or die-to-database comparison these reflectivity variations may greatly degrade the comparison outcome. In other words, as the thickness of the dielectric layer may vary in a manner that is usually unknown to the detection system, the detected signal may be responsive to the unknown thickness of the layer. The detected signal can vary substantially as a result of said unknown thickness thus causing detection errors.

There are known in the art techniques for detecting thin film thickness variations across a wafer (referred to also as non-uniform removal of semiconductor surface) these variation can result from various processes including chemical mechanical polishing (CMP):

U.S. Pat. No. 5,486,129 discloses a system for polishing a semiconductor wafer that includes a rotatable platen subassembly and a drive mechanism coupled to rotate the platen subassembly at a platen velocity. A polishing head supports and holds a face of the semiconductor wafer in contact with the platen subassembly to polish the wafer face whereby individual regions of the wafer face have different polishing rates. The polishing head includes pressure applicators for applying various localized pressures on the individual regions of the semiconductor wafer to conform the wafer face to a selected contour. The system also includes a polish control subsystem for monitoring in situ the polishing rates at various regions of the semiconductor wafer. The polish control subsystem adjusts in situ the platen velocity and/or the individual localized pressures applied to the semiconductor wafer to change the polishing rates of the individual regions of the semiconductor wafer. The system can also be adapted to change other operational parameters, such as wafer velocity, wafer polishing path across the platen, slurry composition and flow rate (for CMP processes), and force applied to the wafer when contacting the platen. A method for polishing a semiconductor wafer is also described.

U.S. Pat. No. 5,486,129 discloses A system for polishing a semiconductor wafer, the system comprising a wafer polishing assembly for polishing a face of a semiconductor wafer at a polishing rate and a polishing uniformity, the wafer polishing assembly including a platen subassembly defining a polishing area, a slurry supply system delivering a slurry to the polishing area, and a polishing head selectively supporting a semiconductor wafer and holding a face of the semiconductor wafer in contact with the platen subassembly; and an optical measurement system measuring film thickness at multiple different locations on the wafer face while the wafer is under a liquid, wherein drying of the wafer is avoided while the measurements are taken.

There is a need in the art to provide for a signal variation measurement technique for detecting thin film thickness variations across an object (such as wafer or reticle) and there is a need to compensate for thin film thickness variations while implementing bright filed inspection.

SUMMARY OF THE INVENTION

The present invention provides a method for measuring thin film thickness variations of inspected wafer that includes an upper non-opaque thin film, comprising:
  a) scanning the wafer and obtain wafer image that includes die images each of which composed of pixels;
  b) identifying at least one region in a first die image and obtain at least one first intensity measurement of the respective region;
  c) identifying corresponding at least one region in a second die image and obtain at least one second intensity measurement of the respective region;
  d) processing the at least one first intensity measurement and the at least one second intensity measurement; to obtain at least one signal variation between said at least one second intensity measurement and said at least one first intensity measurement,
  whereby each signal variation, from among said at least one signal variations, is indicative of thickness variation between a region in the second die and a corresponding region in the first die.

The invention further provides a method for measuring thin film thickness variations of inspected object that includes an upper non-opaque thin film, comprising:
  a) obtaining first intensity measurement of a first die and a second intensity measurement of a second die of a wafer;
  b) calculating first average and standard deviation of a difference between selected corresponding portions of the first intensity measurement and the second intensity measurement;
  c) calculating second average and standard deviation of a difference between selected corresponding portions of the second intensity measurement and the first intensity measurement; and
  d) providing indication on thickness variation depending upon the first average if the first standard deviation is lower than the second standard deviation, otherwise provide indication on thickness variation depending upon the second average.

The invention still further provides a method for measuring thin film thickness variation, comprising:
identifying at least two distinct surface characteristics, and
performing said stages, each time with respect to different surface characteristic from among said at least two distinct surface characteristics.

Still further, the invention provides a method for measuring thin film thickness variation, comprising:
a) detecting reflected light signals to obtain two sets of multiple signal intensities associated with two ideally identical regions of an inspected object that comprises of a upper non-opaque thin film;
b) processing at least a portion of each set to determine signal variations out of the two sets; and
c) utilizing the signal variations to provide an estimation of the thin film thickness.

By a still further aspect the invention provides a system for measuring thin film thickness variations of inspected wafer that includes an upper non-opaque thin film, comprising:
a device for scanning the wafer and obtain wafer image that includes die images each of which composed of pixels, identifying at least one region in a first die image and obtain at least one first intensity measurement of the respective region; and identifying corresponding at least one region in a second die image and obtain at least one second intensity measurement of the respective region;
a processor for processing the at least one first intensity measurement and the at least one second intensity measurement; to obtain at least one signal variation between said at least one second intensity measurement and said at least one first intensity measurement,
whereby each signal variation, from among said at least one signal variations, is indicative of thickness variation between a region in the second die and a corresponding region in the first die.

The invention still further provides a system for measuring thin film thickness variations of inspected object that includes an upper non-opaque thin film, comprising:
a device for obtaining first intensity measurement of a first die and a second intensity measurement of a second die of a wafer;
a processor for calculating first average and standard deviation of a difference between selected corresponding portions of the first intensity measurement and the second intensity measurement;
the processor calculating second average and standard deviation of a difference between selected corresponding portions of the second intensity measurement and the first intensity measurement; and
output device for providing indication on thickness variation depending upon the first average if the first standard deviation is lower than the second standard deviation, otherwise provide indication on thickness variation depending upon the second average.

Still further the invention provides a system for measuring thin film thickness variation, comprising:
a device for detecting reflected light signals to obtain a first set of multiple pixels; the set is associated with a first region of an inspected object that comprises of a upper non-opaque thin film, and for detecting reflected light signals to obtain a second set of multiple pixels associated with a second, ideally identical, region of the object;
a processor for processing the first and second sets to obtain detected signal variations that are indicative of thickness variation between the regions.

Still yet further the invention provides a system for measuring thin film thickness variation, comprising:
a device for detecting reflected light signals to obtain two sets of multiple signal intensities associated with two ideally identical regions of an inspected object that comprises of a upper non-opaque thin film;
a processor for processing at least a portion of each set to determine signal variations out of the two sets; and
an output device for providing an estimation of the thin film thickness. utilizing using the signal variations.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
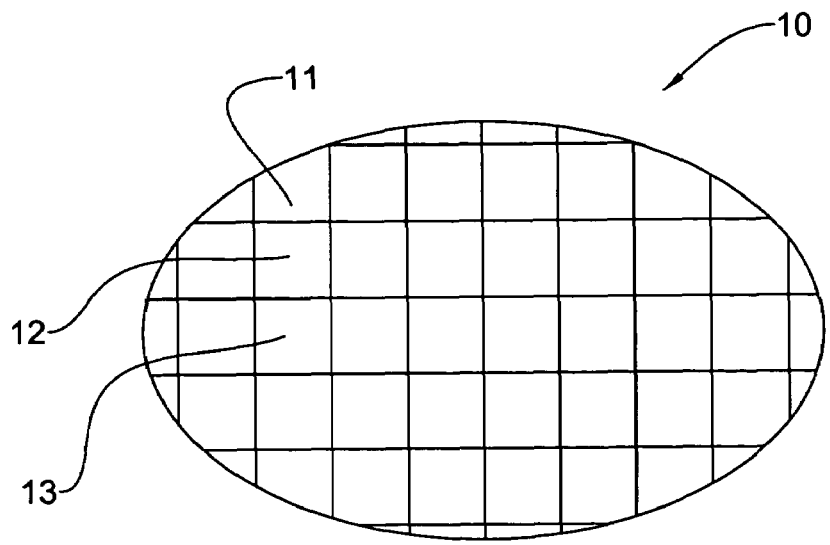
FIG. 1 illustrates schematically a wafer.

Those versed in the art will readily appreciate that the various calculation/processing operations described with reference to specific embodiments of the invention are carried out by a processor. Note that the term processor embraces any processing system including one or more processing devices operating in accordance with the following non limiting variants: serially/parallel/distributed and/or in a single location or remote one with respect to the other and communicating through communication network/link. Other variants are applicable, all as required and appropriate.

Note also that thickness variations, such as those introduced by Chemical Mechanical Planarization (CMP) technique are mapped to detected signal Gray Level (GL) variations between ideally identical pixels.

GL variations (referred to also as detected signal variation) that arise from thickness variations across the wafer are a slow phenomenon compared to pixel changes resulting from defects. Thus, in contrast to gradual detected signal variations that arise from thickness variations, the detected signal variations that stem from "normal" defects are more of abrupt nature which gives rise to noticeable change in the GL value(s) of pixel(s) compared to other pixels the reside in close vicinity thereto, all within the same die.

As is well known, a typical, yet not exclusive, Die-to-Die defect detection scheme is based on subtracting the scanned image of adjacent dies and threshold the result in order to allow a reasonable false defects rate. The detection process can be viewed as subtracting the gray level value of a pixel in the current die image from its best-known predictor. Improving the predictor will result in lower thresholds. In the normal case, the predictor is simply the corresponded Gray level of the previous die image.

Detected signal variation deteriorates the quality of the trivial gray level predictor. Suppose that the gray level variation of some specific layer may vary in range of +/−10 GL. Using the trivial predictor will result in adding 10 GL to the threshold. Since the GL variations is a relatively 'slow' phenomenon, the predictor may be improved by using global statistics, as will be explained in greater detail below. This can be done, in accordance with one embodiment, by measuring how Gray Levels move in average between dies, and subtract the measured value from the Difference (error) image, thereby filtering out the contribution of detected signal variation (due to thickness variation) and allow the Die-to-Die defect detection subsystem to provide more accurate analysis based on input detected signal variation that predominantly stem from defect compared to prior art situations where the input includes not only detected signal variations that relate to defects but also to a "noisy" thickness variation related input.

There follows now a description in connection with various embodiments of the invention. Note that for convenience of description only, the description below refers to certain limiting features. The invention is by no means limited by these limitations. For instance, the description below refers to wafers, however those versed in the art will readily appreciate that the invention applies also to other objects (including but not limited to reticles). Moreover, the description refers to thickness variations that stem from CMP process, however the invention is applicable to other thin film thickness variation. In addition, the description refers to processing of successive dies in a wafer. The invention not bound by this example and accordingly other die do die (not necessary neighboring) or die to database are also applicable. In addition, the description below refers to color measurement and obtaining image of the inspected surface. The invention is applicable also to other intensity measurement techniques, where the result is not necessarily an image, for instance, photomultiplier tubes (PMTs) that provide an array of intensity values but do not provide an image.

Figure 2:
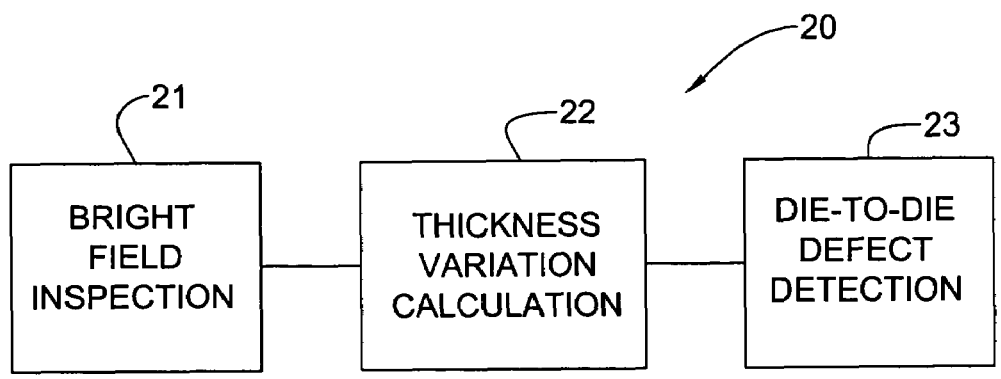
FIG. 2 illustrates schematically general system architecture in accordance with an embodiment of the invention.

Bearing thin in mind, attention is drawn to FIG. 1, showing schematically a wafer 10 that consists of dies of which three are marked, for illustrative purposes, as 11, 12 and 13. FIG. 2 illustrates schematically general system architecture 20 in accordance with an embodiment of the invention. The system includes a Bright Field Inspection sub-system 21 known in the art coupled to thickness variation calculation sub-system 22 which, in turn, is coupled to Die-to-Die defect detection sub-system 23 known in the art.

Bright Field Inspection sub-system 21 is configured, as is known per se, to scan the wafer 10 and obtain a wafer image that includes die images each of which composed of pixels.

The die images include those of exemplary dies 11, 12 and 13. Note that the invention is not bound to the use of inspection sub-system for scanning the wafer and obtain die images and, accordingly, other intensity measurement sub-systems are applicable. The invention is, likewise, not bound to any specific bright field inspection sub-system, or to any specific manner of operation of the latter. For instance, the scanning stage may include scanning of the entire wafer 10 and feeding the scan data (of all dies) to the thickness variation calculation sub-system 22, or by way of another embodiment feeding the scanned data to sub-system 22 on-the-fly e.g. by scanning a die of the wafer (say 11) so as to obtain a die image composed of pixels and feeding the image data to sub-system 22, and thereafter scanning a successive die 12 of the wafer so as to obtain a die image composed of pixels and feeding the image data to sub-system 22, and so forth until the entire wafer is scanned. Other variants are applicable all as required and appropriate.

The thickness variation calculation sub-system 22 operates, by this example, on successive die images in a manner that will be described in detail below, and provides as an output detected signal variation(s) measurements indicative of thickness variations between regions in the successive dies.

Sub-system 22 may be in a stand alone configuration or integrated in sub-system 21.

The detected signal variation(s) data that is indicative of thickness variation(s) may serve for various applications. In accordance with one embodiment the thickness related detected signal variation(s) data obtain in sub-system 22 is fed to a die-to-die defect detection sub-system 23, for detecting defects on the wafer in a known per se manner. Note that the invention is not bound by the use of Die-to-Die defect detection sub-system and accordingly other defect detection sub-systems are applicable. In particular, the invention is not bound by the use of any specific die-to-die defect detection sub-system.

Sub-system 23 may be in a stand alone configuration or integrated in any of or both of sub-systems 21 and 22.

Note also that the invention is not bound by the specific split into distinct three sub-systems as depicted in FIG. 2, and accordingly other system configurations are applicable, depending upon the particular application.

Figure 3:
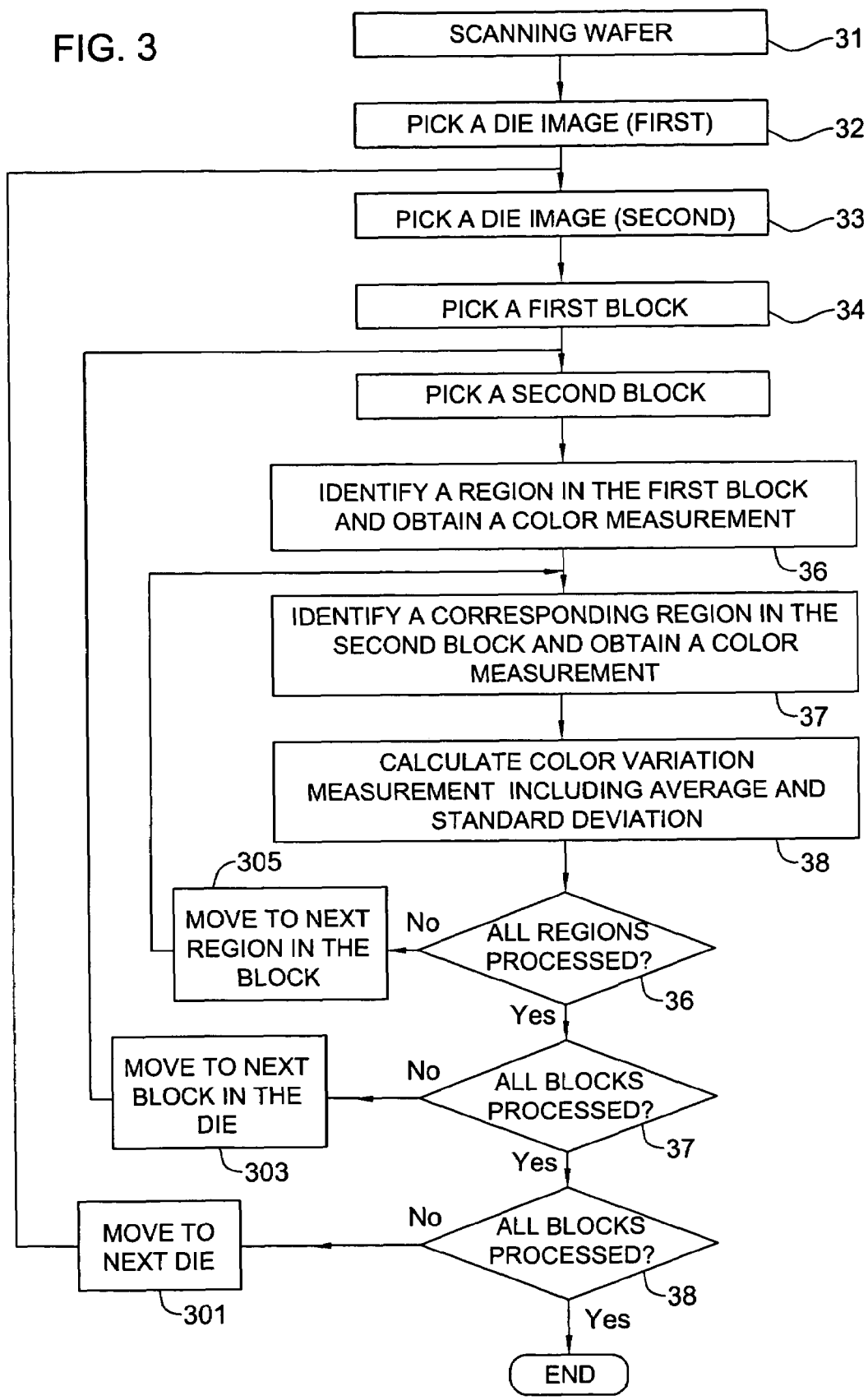
FIG. 3 illustrates a flow diagram of the operational stages of a system in accordance with an embodiment of the invention.

Bearing this in mind, attention is drawn to FIG. 3 illustrating a flow diagram of the operational stages of a system in accordance with an embodiment of the invention. The operational stages of the invention will be explained with reference also to FIG. 4 that illustrates schematically exemplary successive dies 11 and 12 (shown also in FIG. 1).

Figure 4:
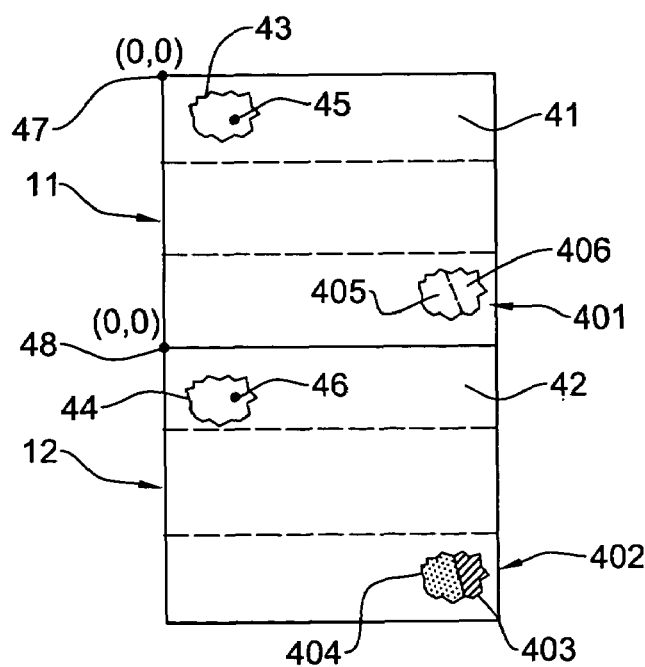
FIG. 4 illustrates schematically exemplary successive dies that are subjected to determination of thickness related detected signal variation, in accordance with the invention.

Thus, in operation, the wafer 10 is scanned in stage 31 (in sub-system 21) to obtain wafer image that includes images of the distinct dies. The image data is fed to the thickness variation calculation sub-system 22. In the latter, a first and second die images are picked (say 11 and 12) in stages 32 and 33. Thereafter, in stages 34 and 35 first and second blocks are picked. FIG. 4 is an enlarged view of dies 11 and 12 and the corresponding blocks are 41 and 42 (by this particular non limiting example in a form of slices—marked in dashed line). Note that each die is broken down to smaller units i.e. blocks (e.g. each block in a form of slice) for convenience of processing. The invention is not bound by a processing that utilizes blocks.

Having identified the blocks, a first region is identified in the first block 36 and its (GL) measurement is obtained. The region is selected to be for example all pixels having the same (or substantially the same) gray level value. For instance, In FIG. 4, region 43 (referred to also as first GL region image) embraces all the pixels with the same GL value, say 5. In the case of e.g. 8 bit GL representation, there are by a specific embodiment up to 256 different GL region images in the block. Note, incidentally, that for simplicity the description with reference to FIG. 3 assumes that the regions are processed one at a time, i.e. all pixels having GL value=1 and thereafter all pixels having GL that=2, etc. This, however, is only one possible example and by way of another example the pixels are processed one at a time and each pixel is "classified" to its corresponding region, depending upon its GL value.

Next, a corresponding region is identified in the second block 37 and the intensity measurement of this region is obtained. Note that the corresponding region is composed of pixels having the same location (offset) in the second die as those of the first region in the first die. The corresponding second GL region image is designated in FIG. 4 as 44. Note that pixel 45 in the first GL region image 43 has the same offset (relative to the init of the first die 47) as its corresponding pixel 46 in the second GL region image 44. The offset of pixel 46 is referred, e.g. relative to the init 48 in the second die. The same correspondence relationships apply to the other pixels in regions 45 and 46.

Note that regions 43 and 44 are ideally identical. Put differently, in the case of fault free wafer (i.e. consisting of identical dies) it would have been expected that all the pixels of the second region image 44 (referred to by this embodiment as Second GL region image) will also have the same GL value as those of the first region 43. Thus, if all pixels of the latter have GL value=5, in the case of fault free wafer all the pixels of the former are also expected to have GL value=5. If, however, a thickness variation is encountered and bearing in mind that thickness variation is a slow changing phenomenon, it may give rise to detected signal variation reflected in the other (including adjacent) dies. Accordingly, by this particular example, due to thickness variation effect some or possibly all the pixels in the corresponding region 44 may have different GL value.

Before moving on, it is noteworthy that the selection of regions with all pixels having (ideally) identical (or substantially identical) GL value is just an example of a broader aspect of the invention. Thus in accordance with a broader aspect two ideally identical regions (not necessarily having all pixels with the same value) of an inspected object (e.g. wafer) are processed. This broader aspect will be discussed in greater detail below.

Reverting now to FIG. 4, the intensity measurement of the corresponding image is obtained 37 (i.e. the gray level values of the pixels that form region 44 (referred to by this embodiment as Second GL region image).

Note, incidentally, that, as before, it is not mandatory to process all pixels in the corresponding region (e.g. 44) and only then move to the next region.

Next, (stage 38), signal variation is calculated in respect of each region. For a better understanding, attention is also drawn to FIGS. 5A-C which are graph representations that pertain to the calculation of average and standard deviation between images, in accordance with an embodiment of the invention.

Figure 5A:
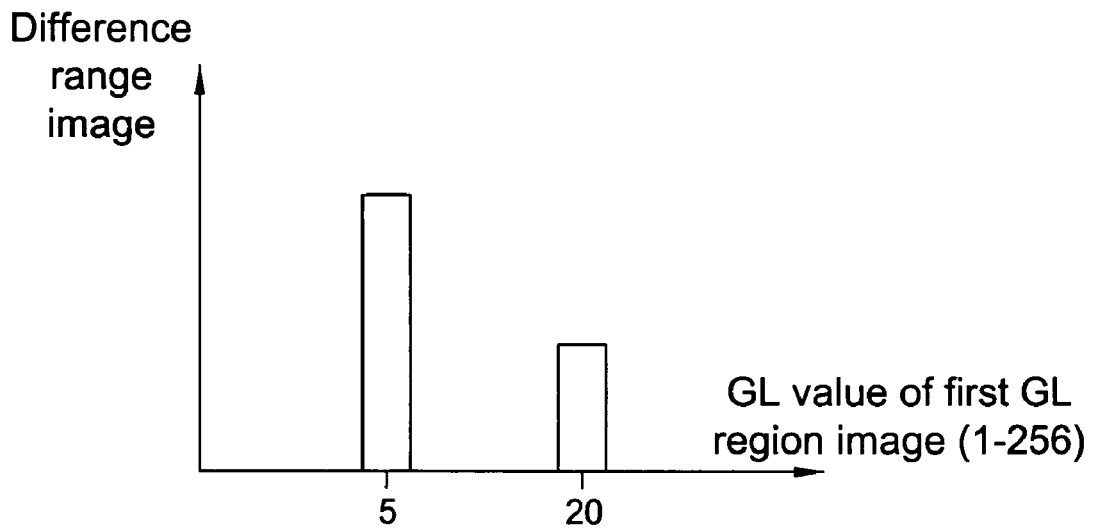
FIG. 5A-C are graph representations that pertains to the calculation of average and standard deviation between images, in accordance with an embodiment of the invention.

FIG. 5A is a histogram where the abscissa indicates GL values of the first GL region images of which the GL values 5 and 20 are shown, (out of possible 256 values for the specific example of 8 bit representation). The ordinate indicates difference region image value. The latter is calculated by subtracting the first GL region image from the second GL region image (and the square of this result is also recorded (see ordinate of FIG. 5C). Reverting to FIG. 5A, more specifically, each GL value of a pixel in the region image 43 (which as may be recalled is composed of pixels having all identical GL value that equals to 5) is subtracted from the GL value of the corresponding pixel in region image 44, and the result is accumulated in the difference region image (ordinate of FIG. 5A). The square of this result is accumulated in the ordinate of FIG. 5C and the counter (shown in the ordinate of the graph representation of FIG. 5B) is incremented. This procedure is repeated in respect of all pixels in the region. Now, assume that no thickness variation is encountered (i.e. two ideally identical regions), it would have been expected that all pixels in the second region image 44 would also have GL value=5, and accordingly the difference result in respect of each pixel would be zero and, likewise, the sum total that is accumulated (and shown in the ordinate of FIG. 5A) would be zero. If, however, thickness variation is encountered (giving rise to detected signal variation) this would be reflected in the value accumulated in the ordinate of FIG. 5A, such that, generally speaking, the more the thickness variation that larger the accumulated total.

Figure 5B:
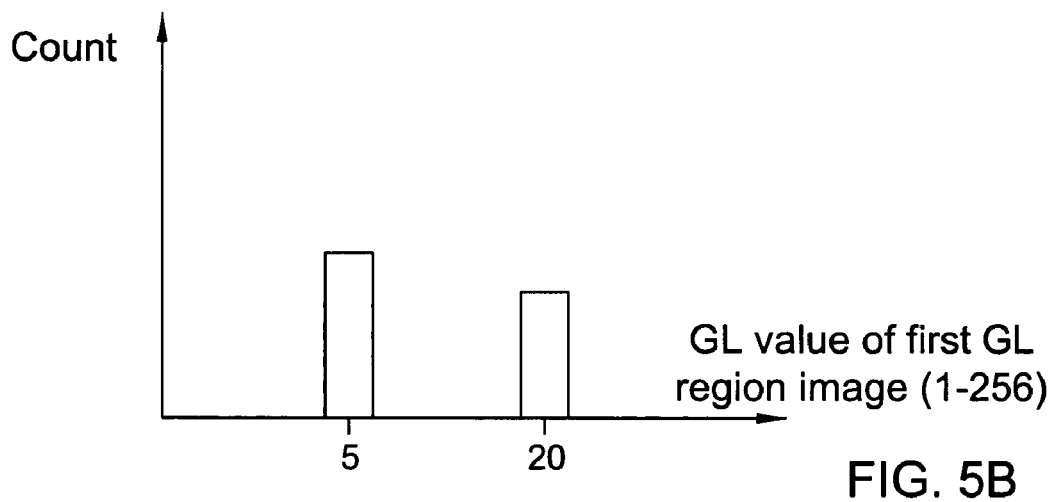
Figure 5C:
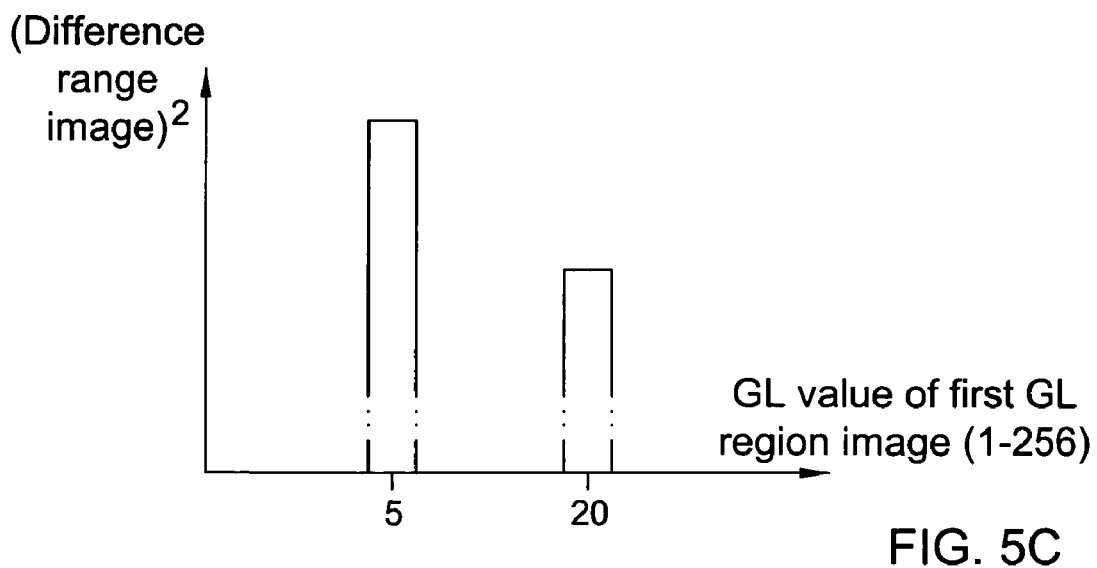

Having calculated the difference region image for the region i=5, an average thereof is calculated (referred to as first average value for the region) by simply dividing the ordinate value for GL=5 (taken from FIG. 5A) by the count value n (for GL=5) taken from the ordinate of FIG. 5B. The standard deviation is also calculated based on the square result accumulated in the ordinate of FIG. 5C. The average and the standard deviation are referred to also as first average value and first standard deviation value, respectively. Now, based on the understanding that thickness variation is a slow changing phenomenon it would have been expected that the average value would indicate on the thickness variation and that the standard deviation would be low. The latter is expected to be low, since all pixels that reside in close proximity to each other (for instance all pixels residing in the same region) are supposed to have identical gray level values or, in other words, the standard variation should be relatively low. If the standard deviation is not low there are good prospects that factors other than thickness variation (due to CMP malfunction) "contributed" to the detected signal variation.

Thus, if detected signal variation is obtained and the standard variation is low, there are good prospects that the contribution due to thickness variation is the calculated average and, accordingly, it can be fed to the die-to-die detection sub-system 23. The latter would filter out this value and would be able to detect defects (if any) in higher accuracy. Note, incidentally, that the invention is not bound by the use of the signal variation value (indicative of thickness variation) in the context of defect detection sub-systems, and accordingly other applications are feasible, all as required and appropriate.

Reverting to FIG. 3, the procedure continues until all regions are processed (39 and 301), all blocks in the die are processed 303 and all dies in the wafer are processed (304 and 305). When all the dies were processed in the manner specified, the process is completed. 306.

Note that the invention is not bound by the specific procedure described with reference to FIG. 3, for calculating detected signal variations.

Thus, by one embodiment, the detected signal variation measurement is based on calculating the following calculation:

Measuring the average mapping of gray levels between two corresponding regions in blocks of successive dies (denoted as First and Second). The measurement part will generate the following statistics (for, say 8 bit GL value):

1. First Average Value[256]: First Average Value[i]=The average Difference region value when First region GL=i.

2. First Standard Deviation value[256]:First Standard Deviation value [i]=The Standard variation of the Difference region value when First region GL=i.

Where Different region value=Second region(i)–First Region (i).

It is accordingly appreciated that two vectors (First Average Value[256], and First Standard Deviation value[256]) are obtained.

By one embodiment, the procedure described with reference to FIG. 3, is calculated separately with respect to distinct surface characteristics. By one embodiment there are two surface characteristics, i.e. edge and non-edge. It has been found that thickness variation would be manifested as different GL values for different surface characteristics. The resulting values would then be fed to the defect detection sub-system along with the surface characteristic indication.

Reverting now to the previous example, when two system characteristics are considered (edge and non-edge) four (instead of two) vectors are obtained, two for the edge category and two for the no-edge category.

As was explained with reference to FIG. 3, if the calculated standard variation is low, there are good prospects that the contribution due to thickness variation is the so calculated average. If, however, the calculated standard deviation exceeds a predetermined threshold, this may indicate that the so calculated average value is not representative of thickness variation. Consider, for example, region 401 in die 11 of FIG. 4, where all pixels have the same GL value, say, j. Viewing the corresponding region 402 of die 12 shows that it is composed of two sub-regions. One (403) marked in hashed lines (composed, for simplicity, of pixels all having substantially the same GL value k) and another 404 marked in dotted line (composed, for simplicity, of pixels all having substantially the same GL value i).

Assume that the GL value k (>j) is close to j and also the GL value i (<j) is close to j (note, however, that k and i are in different polarity relative to j). Accordingly, the first average value (which as recalled obtained by applying average to the difference range image [the latter obtained by subtracting the first GL region image 401 from the second GL region image 402]) is very low. This would seemingly suggest that there is no detected signal variation between the region images (401 and 402) indicating that there is no thickness variation, and accordingly no thickness variation related data will be outputted to the defect detection sub-system, which is obviously undesired.

However, the standard variation is relatively large, (since k and i have different polarity relative to ~j ) and this indicates that the low average should not be interpreted as indicating on small detected signal variation.

What would be desired is to identify that region 401 is, in fact, composed of two sub-regions 405 and 406 and that the detected signal variation measurement between the sub-region 405 and 404 is about i-j (in negative polarity) and that the detected signal variation measurement between the sub-region 406 and 403 is about k-j (in positive polarity). The defect detection sub-system would then apply appropriate filtering and compensate for thickness variations in the appropriate sub-regions.

It should be noted that regions 403 and 404 as well as their respective sub-regions are provided for illustrative purposes only.

Figure 6:
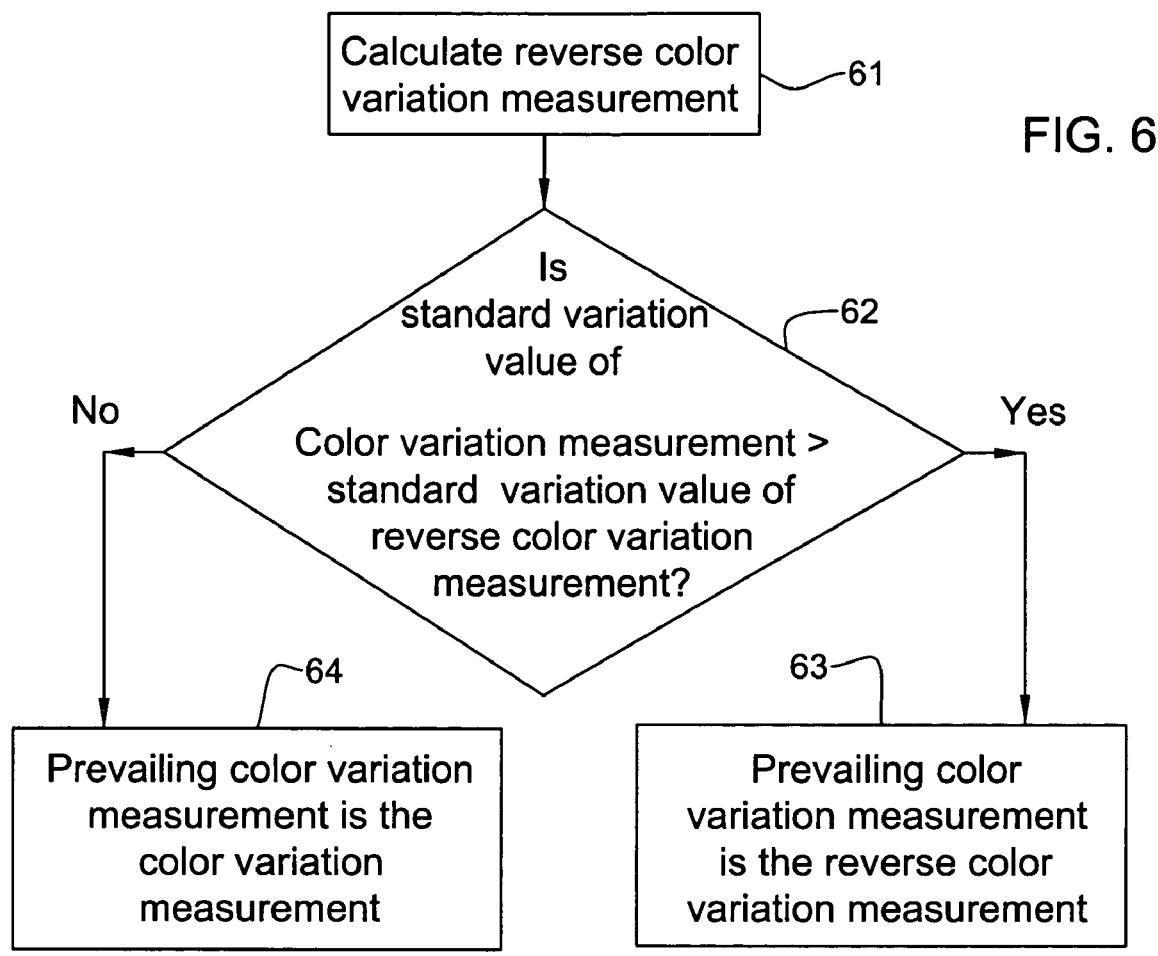
FIG. 6 illustrates a flow diagram of the operational stages of a system in accordance with another embodiment of the invention.

Bearing this in mind, there follows a description of another embodiment of the invention with reference to FIG. 6. Note that certain stages of the present embodiment are performed similar to what has been described above with reference to FIG. 3, and accordingly, whenever applicable, reference is made also to FIG. 3.

Thus, stage 61 calls for calculating a reverse detected signal variation measurement between a first intensity measurement and a second intensity measurement. Note that this in fact is a very similar procedure as described with reference to FIG. 3, however, in reverse, i.e. "starting" with the second die (e.g. 12 in FIG. 4) and identifying distinct regions (e.g. up to 256 in 8 bit GL representation or, e.g. up to 65,536 regions in 16 bit GL representation, etc.) and identify corresponding regions in the first die (e.g. 11 in FIG. 4) and calculate the average and the standard deviation similar to the procedure described above with reference to FIG. 3. As before, the procedure continues until all regions in a block, all blocks in a die and all dies in the wafer are processed.

By one embodiment, certain parts may be skipped (for example certain regions of certain blocks) if a given criterion is met. A non-limiting criterion is: for those regions where low standard deviation result is obtained in the first phase of calculation (as described with reference to FIG. 3, above), avoid a reverse calculation for relevant regions. For instance, if the standard deviation obtained when processing regions 43 and 44 is low (indicating that the so calculated average data is indicative of the sought thickness variation), there is no need to process the pixels that are accommodated in region 44 when the reverse calculation is applied.

Having determined reverse detected signal variations measurement, it is required to determine a so called prevailing detected signal variation measurement from among the detected signal variation measurement (obtained in the first cycle of calculation, as described e.g. with reference to FIG. 3) and the reverse detected signal variation measurement obtained in the second cycle of calculation (e.g. 61). The "prevailing" one would be determined by comparing (62) the standard variation values of the detected signal variation measurement and the corresponding reverse detected signal variation measurement, and selecting the prevailing one according the lower standard variation value.

Thus, for instance, for regions 43 and 44, the prevailing one would probably be the detected signal variation measurement obtained in the first cycle since the calculated standard deviation thereof was low. Accordingly, the so calculated first average value (for regions 43 and 44) would indicate on the thickness variation (see, e.g. 63 in FIG. 6). In contrast, for regions 401 and 402, the standard variation obtained in the first cycle of calculation was high, and the one obtained in the calculation the reverse signal variation measurement is lower and accordingly the prevailing detected signal variation measurement is the reverse detected signal variation measurement (64).

Note that in the reverse detected signal variation measurement, region 402 belongs to two distinct regions, i.e. 403 (and possibly supplemental region with pixels having GL value=k, not shown in FIG. 4) and 404 (and possibly supplemental region with pixels having GL value=i, not shown in FIG. 4). The standard deviation value for region 404 (and its corresponding region in Die 11) and the standard deviation value for region 403 (and its corresponding region in Die 11) are relatively small and therefore the prevailing detected measurement is the one obtained in the second cycle of processing for the reverse detected signal variation measurement.

Having identified the prevailing detected signal variation, the relevant average value is the one indicative of the thickness variation and can be fed to the defect detection sub-system. For instance, for regions 403 (and its corresponding region in die 11) the average value would be k-j (in positive polarity) and for regions 404 (and its corresponding region in die 11) the average value would be i-j (in negative polarity). The defect detection sub-system (e.g. 23) would then be able to duly filter-out the "contribution" of the thickness variation when processing the image data for revealing defects.

As before, the reverse calculation may apply separately to different characteristics such as edge and non-edge.

In accordance with a specific embodiment, the reverse calculation includes:

(i) calculating Second average value (i) being an average of reverse difference region image for region (i), where reverse difference region image for region (i) being a result of subtracting said Second GL region image (i) (e.g. region 404) from said First GL region image (i) (e.g. 405);

(ii) calculating Second standard deviation value (i) being a standard deviation of said reverse difference region image for region (i);

said Second average value (i) and Second standard deviation value (i) stand for said reverse detected signal variation measurement of said region (i) stipulated above.

(iii) determining at least one prevailing detected signal variation measurement; each prevailing detected signal variation measurement is selected from either a detected signal variation measurement or corresponding reverse detected signal variation measurement, as follows:

comparing the First standard deviation value (i) of the detected signal variation measurement and the Second standard deviation value (i) of corresponding reverse detected signal variation measurement, and selecting the prevailing detected signal variation measurement according a lower standard variation value from among said First standard deviation value (i) and Second standard deviation value (i);

whereby, each prevailing detected signal variation measurement, from among said at least one prevailing detected signal variation measurement, is indicative of (i) thickness variation between a region in a block in the second die and a corresponding region in a block in the first die, or (ii) thickness variation between a region in a block in the first die and a corresponding region in a block in the second die, which the case may be.

For convenience, the description above focused in obtaining average dada (indicative of thickness variation) of detected signal variation measurement, where the latter is obtained as difference between intensity measurements of images in successive dies. This is by no means binding. Thus, for example, other parameters (in addition to the average) can be used for obtaining thickness variation indication. By way of another non-limiting example, the detected signal variation data is gathered not necessarily only from two consecutive dies, for instance, by using additional data (such as average data) obtained also form previously processed dies, etc.

Figure 7:
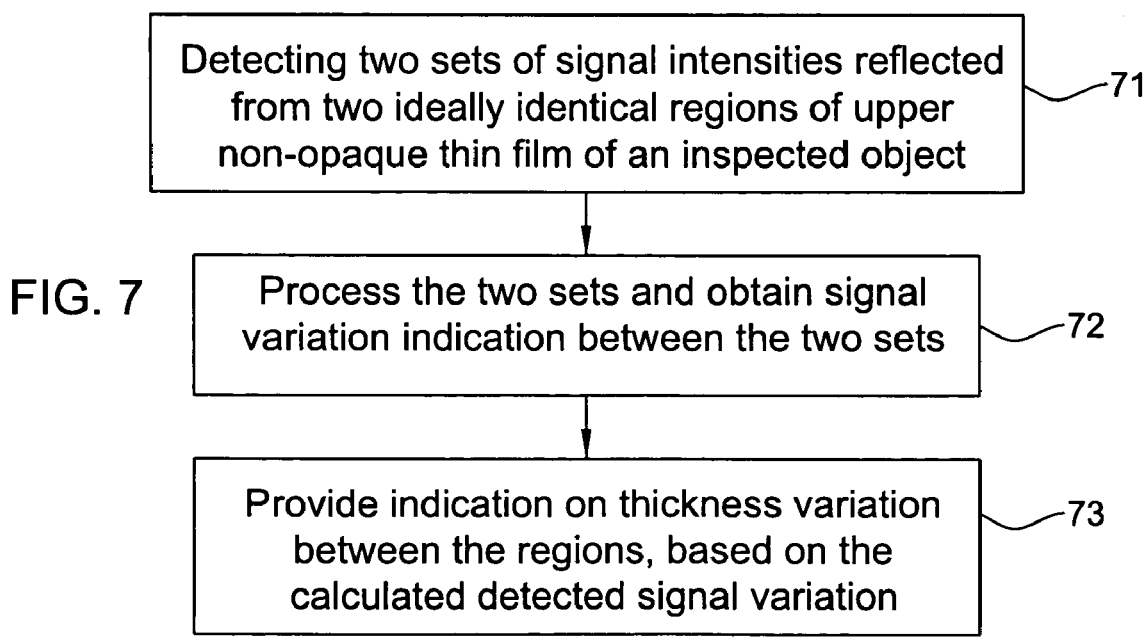
FIG. 7 illustrates a flow diagram of the operational stages of a system in accordance with an aspect of the invention.

Turning now to FIG. 7, there is shown a flow diagram of the operational stages of a system in accordance with a broad aspect of the invention. Thus, stage 71 includes detecting two sets of signal intensities reflected from two ideally identical regions of upper non-opaque thin film of an inspected object. A non-limiting example of an object is a wafer. A non-limiting example of the two regions is two regions in successive dies. Other variants are applicable, such as non consecutive dies, die and database, etc. A non-limiting example of a region (from among the two ideally identical sets) is one with identical signal intensities (i.e. pixels having all the same GL value). This, however, is not binding and other arbitrary regions non necessarily accommodating pixels of identical intensity, can also be processed in accordance with this aspect of the invention.

Next, in stage 72, the two sets are processed to obtain signal variation indication between them; and there is provided an indication on thickness variation between the regions, based on the calculated detected signal variation (73).

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

In the following claims, alphabetic characters, numeral and roman numerals are used for convenience only to designate stages and accordingly they do not necessarily imply on a specific order of the stages.

The present invention has been described with a certain degree of particularity, but those versed in the art will readily appreciate that various alterations and modifications may be carried out without departing from the scope of the following Claims.

The invention claimed is:

1. A method for measuring thin film thickness variations of an inspected wafer that includes an upper non-opaque thin film, comprising:

a) scanning the wafer and obtaining a wafer image that includes die images, each of which is composed of pixels;

b) identifying at least one region in a first block of a first die image and obtaining at least one first intensity measurement of the respective region;

c) identifying a corresponding at least one region in a second block of a second die image and obtaining at least one second intensity measurement of the respective region;

d) processing the at least one first intensity measurement and the at least one second intensity measurement to obtain at least one signal variation between said at least one second intensity measurement and said at least one first intensity measurement, whereby each signal variation, from among said at least one signal variations, is indicative of a thickness variation between a region in the second die and a corresponding region in the first die; and further comprising determining a first GL region image (i) being gray level (GL) values of all pixels that constitute a region (i) from among n regions 1 . . . n of said first block; the GL values of all said pixels being equal to i; said first GL region image (i) being said first intensity measurement of a region recited in (b) above;

determining a second GL region image (i) being gray level (GL) values of all pixels that constitute a corresponding region (i) from among n corresponding regions 1 . . . n of said second block; said second GL region image (i) being said second intensity measurement of a region recited in (c) above;

calculating a first average value (i) being an average of difference region images for region (i), where difference region images for region (i) are a result of subtracting said first GL region image (i) from said second GL region image (i); and calculating a first standard deviation value (i) being a standard deviation of said difference region images for region (i); said first average value (i) and first standard deviation value (i) being said detected signal variation measurement between said second intensity measurement and said first intensity measurement of said region (i) recited in (d) above.

2. The method according to claim 1, wherein the intensity measurements of the region in the first die, recited in (b) are all substantially identical.

3. The method according to claim 1, wherein stage (a) includes: (1) scanning a first die of the wafer so as to obtain a first die image composed of pixels; (2) scanning a second, successive, die of the wafer, so as to obtain a second die image composed of pixels.

4. The method according to claim 1, wherein said first and second blocks are slices of a die at predetermined width.

5. The method according to claim 1, further comprising: performing repeatedly said stages (b) to (d), each time with respect to different blocks in the first die image and the second die image.

6. The method according to claim 5, further comprising: after processing all blocks in the first die image and the second die image, performing repeatedly said stages (b) to (d), each time with respect to different first die image and second die image.

7. The method of claim 1, wherein said n being any of 256 or 65,536.

8. The method according to claim 1, further comprising outputting said at least one detected signal variation measurement to a defect detection sub-system.

9. The method according to claim 8, wherein said defect detection subsystem being a die to die defect detection sub-system.

10. The method according to claim 1, further comprising outputting to a die-to die defect detection module said detected signal variation measurement of any region i, from among n regions 1 . . . n, only if said first standard deviation value (i) drops below a predefined threshold.

11. The method according to claim 1, further comprising: identifying at least two distinct surface characteristics, and performing said stages (b) to (d), each time with respect to different surface characteristic from among said at least two distinct surface characteristics, giving rise to distinct at least one detected signal variation for each surface characteristic.

12. The method according to claim 11, wherein said surface characteristics include: edge and non-edge.

13. The method according to claim 1, further comprising outputting said at least one detected signal variation measurement for a die-to-die defect detection.

14. The method according to claim 1, further comprising: identifying at least two distinct surface characteristics; and calculating said First GL region image (i), Second GL region image (i), First average value (i), Second average value (i), for any one of said at least two distinct surface characteristics.

15. The method according to claim 14, wherein said surface characteristics include: edge and non-edge.

16. A method for measuring thin film thickness variations of an inspected wafer that includes an upper non-opaque thin film, comprising:
(a) scanning the wafer and obtaining a wafer image that includes die images, each of which is composed of pixels;
(b) identifying at least one region of a first die image and obtaining at least one first intensity measurement of the respective region;
(c) identifying a corresponding at least one region of a second die image and obtaining at least one second intensity measurement of the respective region;
(d) processing the at least one first intensity measurement and the at least one second intensity measurement to obtain at least one signal variation between said at least one second intensity measurement and said at least one first intensity measurement;
(e) calculating at least one detected reverse signal variation measurement between said at least one first intensity measurement and said at least one second intensity measurement, each one of said detected reverse signal variations measurements expressed as an average and standard variation;
(f) determining at least one prevailing detected signal variation measurement; each prevailing detected signal variation measurement selected from either a detected signal variation measurement or corresponding detected reverse signal variation measurement, as follows: comparing the standard variation values of the detected signal variation measurement and the corresponding detected reverse signal variation measurement, and selecting the prevailing detected signal variation measurement according the lower standard variation value;
whereby, each prevailing detected signal variation measurement, from among said at least one prevailing detected signal variation measurement, is indicative of (i) thickness variation between a region in the second die and a corresponding region in the first die, or (ii) thickness variation between a region in the first die and a corresponding region in the second die.

17. The method according to claim 16, further comprising outputting said at least one prevailing detected signal variation measurement to a defect detection sub-system.

18. The method according to claim 17, wherein said defect detection subsystem being a die-to-die defect detection sub-system.

19. The method according to claim 16, further comprising: identifying at least two distinct surface characteristics, and performing said stage (e), each time with respect to a different surface characteristic from among said at least two distinct surface characteristics, giving rise to distinct at least one detected reverse signal variation for each surface characteristic.

20. A method for measuring thin film thickness variations of an inspected object that includes an upper non-opaque thin film, comprising:
a) obtaining a first intensity measurement of a first die and a second intensity measurement of a second die of a wafer;
b) calculating first average and standard deviation of a difference between selected corresponding portions of the first intensity measurement and the second intensity measurement;
c) calculating second average and standard deviation of a difference between selected corresponding portions of the second intensity measurement and the first intensity measurement; and
d) providing an indication on thickness variation depending upon the first average if the first standard deviation is lower than the second standard deviation, otherwise providing an indication on thickness variation depending upon the second average.

21. The method according to claim 20, further comprising: identifying at least two distinct surface characteristics, and performing said stages, each time with respect to different surface characteristic from among said at least two distinct surface characteristics.

22. The method according to claim 21, wherein said surface characteristics include: edge and non-edge.

23. The method according to claim 20, further comprising outputting said indication on thickness variation to a defect detection sub-system.

24. The method according to claim 23, wherein said defect detection subsystem is a die-to-die defect detection sub-system.

25. A system for measuring thin film thickness variations of an inspected object that includes an upper non-opaque thin film, comprising:

a device for obtaining a first intensity measurement of a first die and a second intensity measurement of a second die of a wafer;

a processor for calculating first average and standard deviation of a difference between selected corresponding portions of the first intensity measurement and the second intensity measurement and second average and standard deviation of a difference between selected corresponding portions of the second intensity measurement and the first intensity measurement; and an output device for providing an indication on thickness variation depending upon the first average if the first standard deviation is lower than the second standard deviation, otherwise providing an indication on thickness variation depending upon the second average.

* * * * *